US009262586B2

(12) United States Patent
Steiger et al.

(10) Patent No.: US 9,262,586 B2
(45) Date of Patent: Feb. 16, 2016

(54) REPRESENTATION OF LARGE, VARIABLE SIZE DATA SETS ON SMALL DISPLAYS (75) Inventors: Bernd Steiger, Roemerberg (DE); Michael Brossart, Germersheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1222 days.

(21) Appl. No.: 12/973,011

(22) Filed: Dec. 20, 2010

(65) Prior Publication Data

US 2012/0157806 A1 Jun. 21, 2012

(51) Int. Cl.
*A61B 5/00* (2006.01)
*G06F 19/00* (2011.01)
*A61B 5/145* (2006.01)

(52) U.S. Cl.
CPC ........ *G06F 19/3406* (2013.01); *A61B 5/14532* (2013.01); *G06F 19/3456* (2013.01)

(58) Field of Classification Search
USPC ................ 600/345, 347, 365; 345/440, 440.1
See application file for complete search history.

(56) References Cited

U.S. PATENT DOCUMENTS

| 7,440,786 | B2 | 10/2008 | Hockersmith et al. | |
|---|---|---|---|---|
| 7,574,069 | B2 | 8/2009 | Setlur et al. | |
| 2006/0281985 | A1* | 12/2006 | Ward et al. | 600/365 |
| 2007/0208244 | A1* | 9/2007 | Brauker et al. | 600/365 |
| 2007/0208246 | A1 | 9/2007 | Brauker et al. | |
| 2008/0119705 | A1 | 5/2008 | Patel et al. | |
| 2009/0271729 | A1 | 10/2009 | Killoren Clark et al. | |
| 2010/0174553 | A1 | 7/2010 | Kaufman et al. | |
| 2010/0299075 | A1 | 11/2010 | Li et al. | |
| 2011/0009813 | A1 | 1/2011 | Rankers | |

FOREIGN PATENT DOCUMENTS

EP 1918837 A1 5/2008

OTHER PUBLICATIONS

Tak-Chung Fu et al's "Progressive time series visualization in a mobile environment", Computers and Communications, 2004 Proceedings, IEEE, vol. 2, pp. 662-667 (2004).

* cited by examiner

*Primary Examiner* — Michael D'Angelo
*Assistant Examiner* — Christian Jang
(74) *Attorney, Agent, or Firm* — Harness Dickey (57) ABSTRACT

A method of enhancing readability of a graph showing glucose values received from a continuous glucose monitoring device (CGM) on the display of a handheld device includes receiving a plurality of CGM glucose values separated by a first fixed time interval. A second fixed time interval at which to display at least a portion of the plurality of CGM glucose values is received. The second fixed time interval is greater than the first fixed time interval. A computer processor of the handheld device determines a characteristic CGM glucose value at a preselected fixed time for each of a sequence of second fixed time intervals within a patient-specified time period. Each characteristic CGM glucose value is derived from two or more received CGM values centered about the preselected fixed time in the corresponding second fixed time interval. The characteristic CGM glucose values for a patient-selected period of time on the display.

12 Claims, 8 Drawing Sheets

REPRESENTATION OF LARGE, VARIABLE SIZE DATA SETS ON SMALL DISPLAYS

FIELD

The present disclosure relates to a continuous glucose monitor (CGM) in communication with a handheld diabetes manager and, more particularly, to various graphical representations of glucose values received from the CGM on the display of the hand held diabetes manager.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise and lifestyle. Lab test results include HbA1C, cholesterol, triglycerides, and glucose tolerance. Healthcare professional recommendations include prescriptions, diets, test plans, and other information relating to the patient's treatment.

Patients using continuous glucose monitors (CGM) generally review summaries of the fluctuations in their glucose values for particular time intervals ranging from hours to days. In particular, a patient wears a CGM that can communicate with a handheld device such as a CGM monitor or a handheld diabetes manager. Because of the relative small screens of the handheld devices, there is a need to process the stream of data received from the CGM, such that a graphical representation that preserves the essential character of the variation of the bG over the selected interval is accurately and clearly represented without artificial distortions. The present teachings are directed to various methods of processing and representing glucose data from a CGM on a small display of a handheld diabetes device, such as a handheld diabetes monitor.

SUMMARY

This section provides a general summary of the disclosure, and is not a comprehensive disclosure of its full scope or all of its features.

The present teachings provide a method of enhancing readability of a graph showing glucose values received from a continuous glucose monitoring device (CGM) on the display of a handheld device. The method includes receiving a plurality of CGM glucose values separated by a first fixed time interval. A second fixed time interval at which to display at least a portion of the plurality of CGM glucose values is received. The second fixed time interval is greater than the first fixed time interval. A computer processor of the handheld device determines a characteristic CGM glucose value at a preselected fixed time for each of a sequence of second fixed time intervals within a patient-specified time period. Each characteristic CGM glucose value is derived from two or more received CGM values centered about the preselected fixed time in the corresponding second fixed time interval. The characteristic CGM glucose values for a patient-selected period of time can be represented in a glucose curve on the display.

In some embodiments, each characteristic CGM glucose value is the median of received CGM glucose values centered about the preselected fixed time for each second fixed time interval. In some embodiments, the first fixed time interval is one minute and the second fixed time interval is five minutes.

The characteristic CGM glucose values at the corresponding preselected fixed times can be stored in a memory module of the handheld device. The received CGM glucose values and the determined characteristic CGM glucose values can be stored in a buffer for a sixty-minute time interval for quick retrieval and for real time display.

Any initial CGM values that are received and do not belong to the second fixed interval that is centered about the predetermined fixed time can be omitted when determining the characteristic CGM glucose value of the second fixed time interval.

A plurality of supporting pixel points for displaying the characteristic CGM glucose values on a display graph of a requested time period for display on the handheld device can be determined from a pixel width of the graph and a time period to be displayed.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

Figure 1:
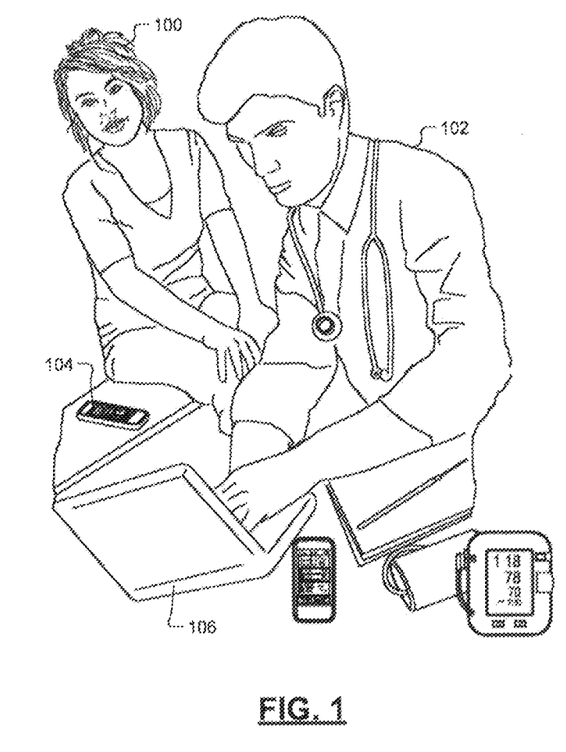
FIG. 1 shows a patient and a treating clinician.

Referring now to FIG. 1, a person 100 with diabetes and a healthcare professional 102 are shown in a clinical environment. Persons with diabetes include persons with metabolic syndrome, person with pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
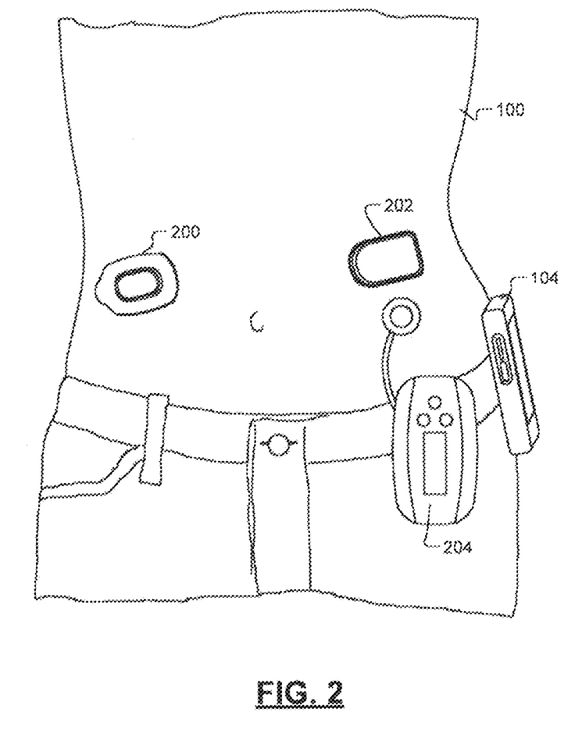
FIG. 2 shows a patient with a continuous glucose monitor (CGM), an ambulatory durable insulin infusion pump, an ambulatory non-durable insulin infusion pump, and a diabetes manger.
Figure 5:
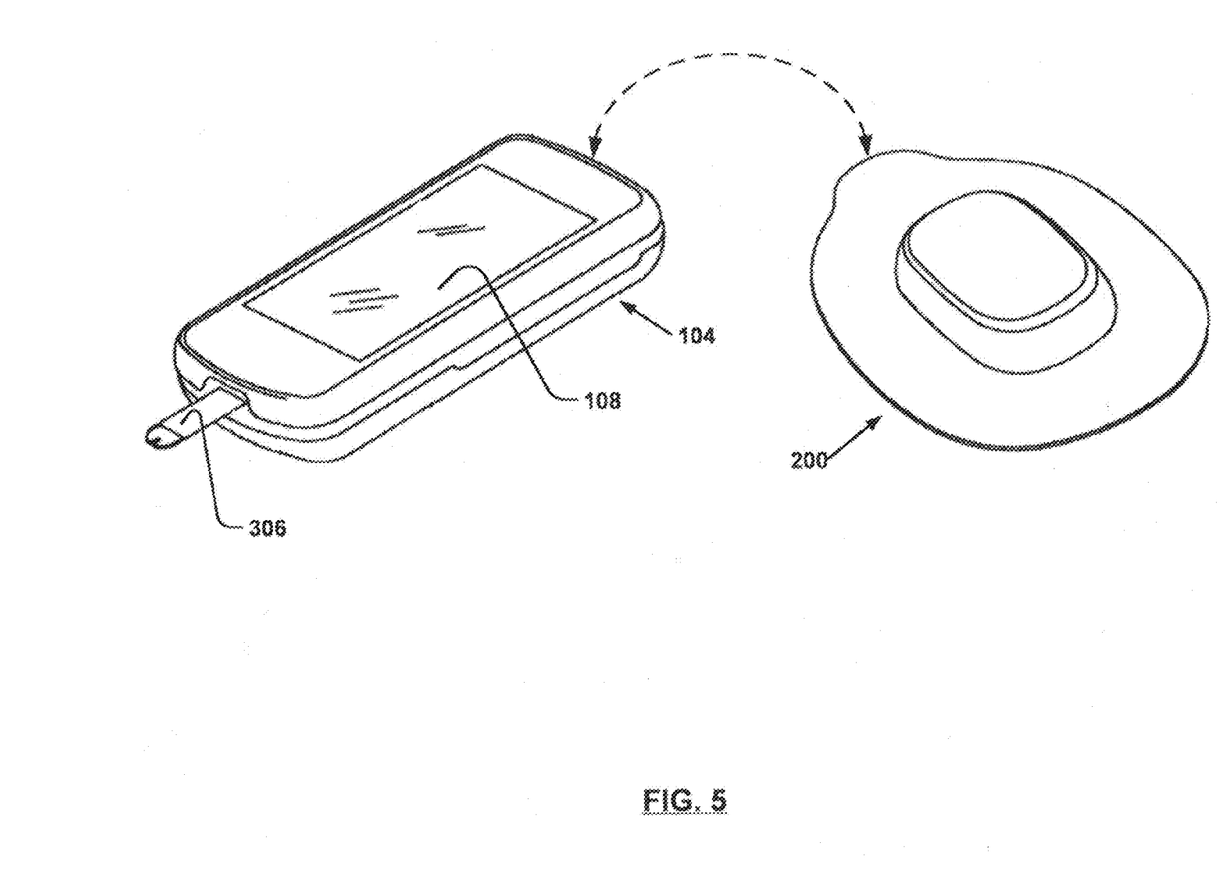
FIG. 5 shows a diabetes manager in communication with a continuous glucose monitor (CGM)

Referring now to FIG. 2, the patient 100 can use a continuous glucose monitor (CGM) 200, an ambulatory non-durable insulin infusion pump 202 or an ambulatory durable insulin infusion pump 204 (hereinafter insulin pump 202 or 204), and the handheld diabetes management device 104 (hereinafter the diabetes manager 104). The CGM 200 uses a subcutaneous sensor to sense and monitor the amount of glucose in interstitial fluid of the patient 100 and communicates corresponding data to the diabetes manager 104, as illustrated in FIG. 5.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives data from the CGM 200 from which glucose levels of the patient 100 are computed. The diabetes manager 104 transmits instructions to the insulin pump 202 or 204, which delivers insulin to the patient 100. Insulin can be delivered in a scheduled manner in the form of a basal dose, which maintains a predetermined insulin dose to the patient 100. Additionally, insulin can be delivered in the form of a bolus dose, which raises the amount of insulin delivered to the patient 100 by a predetermined amount.

Figure 3:
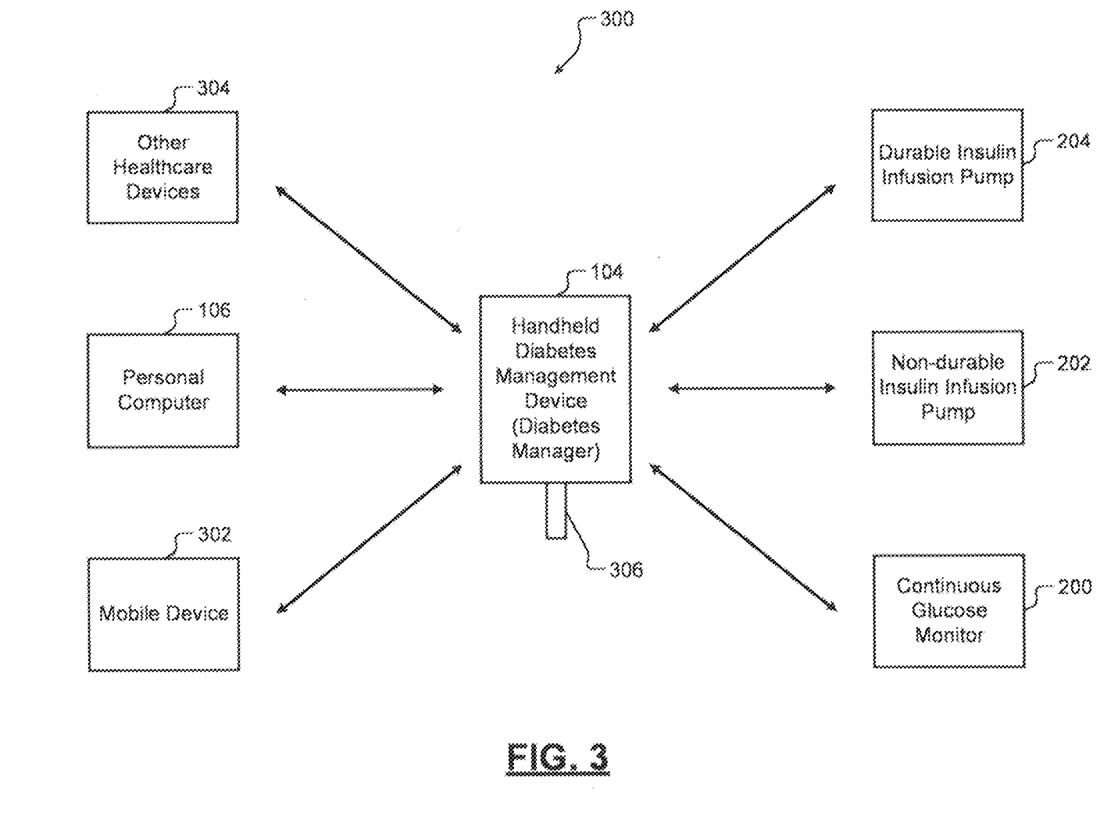
FIG. 3 shows a diabetes management system used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the PC 106 with the diabetes analysis software, and other healthcare devices 304. The diabetes manager 104 is configured as a system hub and communicates with the devices of the diabetes management system 300. Alternatively, the mobile device 302 can serve as the system hub. Communication between the devices in the diabetes management system 300 can be performed using wireless interfaces (e.g., Bluetooth) and/or wireline interfaces (e.g., USB). Communication protocols used by these devices can include protocols compliant with the IEEE 11073 standard, as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive glucose readings from one or more sources (e.g., from the CGM 200). The CGM 200 continuously monitors the glucose level of the patient 100. The CGM 200 periodically communicates data to the diabetes manager 104 from which the diabetes manager 104 computes glucose levels of the patient. The diabetes manager 104 and the CGM 200 communicate wireles sly using generally a proprietary wireless protocol, such as, for example, the Gazell wireless protocol developed by Nordic Semiconductor, Inc, Sunnyvale, Calif. Any other suitable wireless protocol can be used instead.

Additionally, the diabetes manager 104 includes a blood glucose meter (BGM) and a port that communicates with the BGM (not shown). The port can receive a blood glucose measurement strip 306. The patient 100 deposits a sample of blood on the blood glucose measurement strip 306. The BGM analyzes the sample and measures the blood glucose level in the sample. The blood glucose level measured from the sample and/or the glucose level computed using data received from the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

Figure 4:
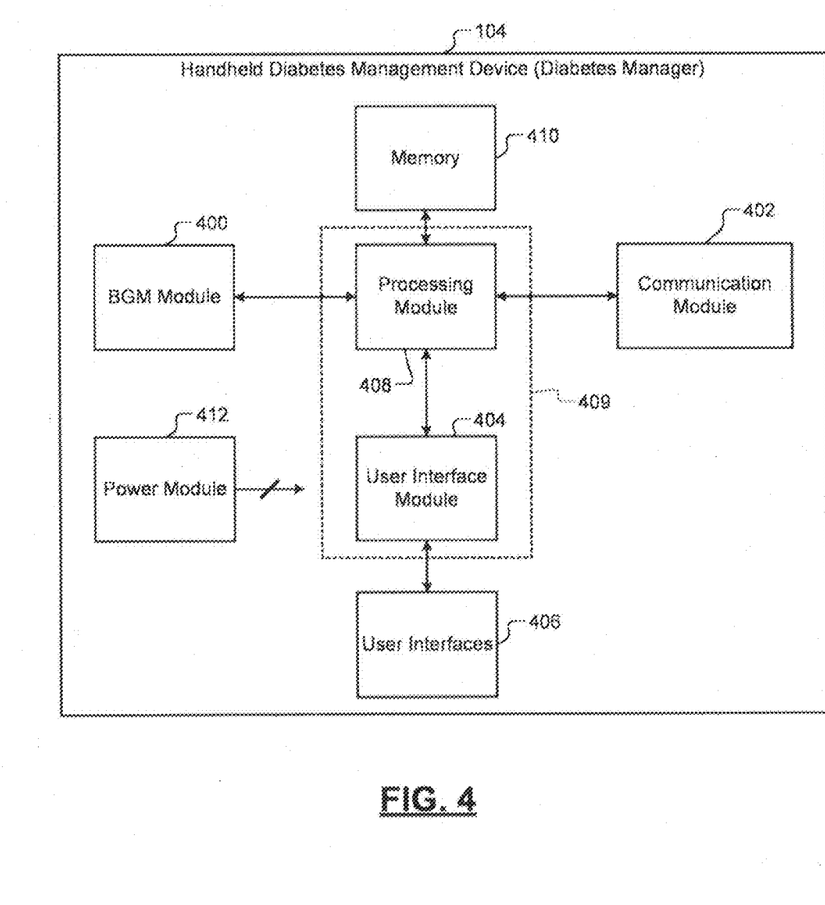
FIG. 4 is a functional block diagram of a diabetes manager.

Referring now to FIG. 4, the diabetes manager 104 comprises a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 includes a rechargeable battery. The battery can be recharged using an adapter that plugs into a wall outlet. The battery can also be charged via the USB port of the diabetes manager 104.

Referring to FIG. 5, an exemplary diabetes manager 104 is illustrated in communication with a continuous glucose monitor 200. The continuous glucose monitor 200 can be used to obtain time-resolved data to identify fluctuations and trends that would otherwise go unnoticed with spot monitoring of blood glucose levels and standard HbA1c tests, such as low overnight glucose levels, high blood glucose levels between meals, early morning spikes in blood glucose levels, and how diet and physical activity affect blood glucose along with the effect of therapy changes. An example of a continuous glucose monitor 200 is shown in U.S. Pat. No. 7,389,133 assigned to Roche Diagnostics Operations, Inc., which is hereby incorporated by reference.

The continuous glucose monitor 200 may receive calibration information and start-up information from the diabetes manager 104. The diabetes manager 104 may receive from the continuous glucose monitor 200 measured CGM glucose values that are subsequently displayed and/or stored on the diabetes manager 104. Blood glucose data may be transmitted from the continuous glucose monitor 200 on demand, or substantially continuously whenever a measurement is carried out by the continuous glucose monitor 200, for example, every minute or every few minutes. Alternatively, the continuous glucose monitor 200 may include a memory and temporarily store measured CGM glucose values which are subsequently transmitted to the diabetes manager 104. For example, the stored values may be transmitted when the memory of the continuous glucose monitor 200 is full, or when a communication is established for other reasons, or in pre-defined time intervals. The continuous glucose monitor 200 may communicate with the diabetes manager wirelessly via an RF data interface, for example short range RF data interfaces based on the Bluetooth standard.

Although a sensor of the continuous glucose monitor 200 may take measurements every second, the sixty data points measured within a minute timeframe can be compressed by taking either the mean or median or other characteristic value of the sixty measurements. Other useful parameters for the minute time range may also be calculated in the continuous glucose monitor 200, including the standard deviation and other trends. The raw data may also be filtered to remove noise or other non-physiological spikes in the data. The compressed and/or filtered data corresponding to each minute, i.e., the characteristic value for each minute, are then transferred to diabetes manager 104.

According to the present teachings, the data or characteristic values received each minute from the continuous glucose monitor 200 are further processed in the diabetes manager 104. The additional processing facilitates the graphical display of the glucose values in a form easily and conveniently presented for the patient in a graph that showcases trends and other important features without cumbersome cluttering and overlapping. In this regard, the diabetes manager 104 includes a screen display 108 that that can be operably connected to the processing module 408 for generally displaying text, graphics, icons, and other objects relating to the operation of the diabetes manager, including a graphical representation of the data received by the continuous glucose monitor 200. The screen display 108 can be an LCD display, a touch screen display, an e-ink display or other type of display that can be used with handheld consumer electronic devices. The screen display 108 can have a resolution or a pixel density that is adequate for displaying graphical representations of the data after processing according to the present teachings.

Figure 6:
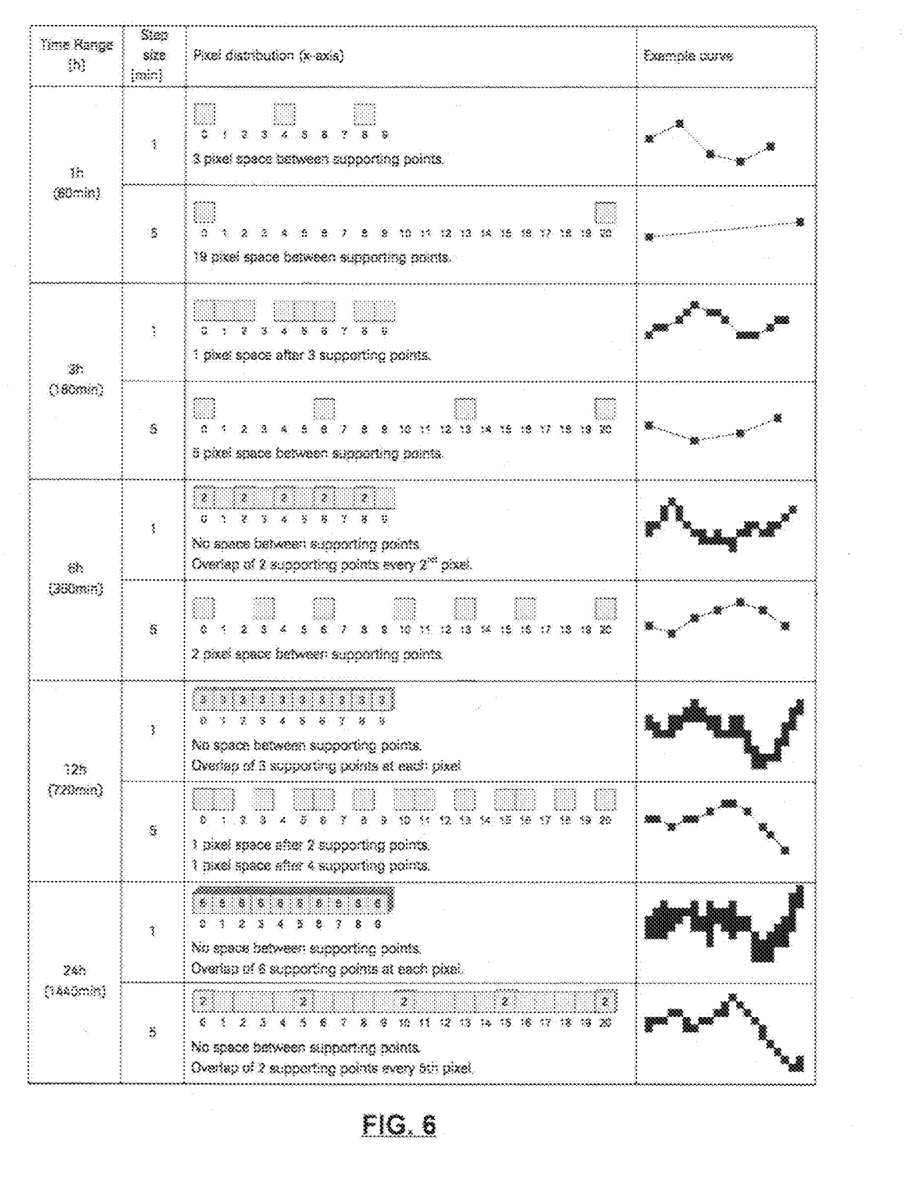
FIG. 6 illustrates various exemplary glucose graphical representations in the display of the diabetes manager for various pixel distribution in time ranges from one hour to twenty-four hours.

According to the present teachings, although the CGM glucose values that are received by the diabetes manage 104 are separated by a first time interval or first step size, a second time interval or step size is selected for better representation depending on the pixel density and size of the screen display of the diabetes manager. The second step size is greater than the first. The first step size can be equal to the minimum received step size, i.e., one minute or greater than one minute. FIG. 6 illustrates exemplary pixel distribution and graphical representation of data for time ranges 1 hour (60 min), 3 hours (180 min), 6 hours (360 min), 12 hours (760 min) and 24 hours (1440 min). A width of 240 pixels is used in these examples. For each time range (1 h, 3 h, etc,) two step sizes are compared: a step size of 1 minute, which corresponds to the step size of the data received from the continuous glucose monitor 200, and a step size of 5 minutes. For a 60 minute time range and one minute step size, the sixty CGM glucose values can fall on every fourth pixel (240/60=4), i.e., the supporting points along the time axis (x-axis) of the graphical representation can be spaced apart with a three pixel space. In contrast, when a step size of five minutes is selected there are 12 supporting points (60/5=12), and the supporting points fall on each $20^{th}$ pixel (240/12=20) and they are separated by 19 pixels. Additionally, it is desirable to maintain all the supporting points corresponding to an earlier range when adding supporting points for the next range. For example, the supporting points 0, 4, 8, etc., that correspond to time step of 1 minute and time range of 1 hr, will also be maintained for the same time step in time ranges of 2 hours, three hours, etc. Similarly, for the time step of 1 minute, supporting points 0 and 20 of the one hour time range will be maintained for all the subsequent greater time ranges.

As the time range for representing the data increases, the pixel space or separation between supporting points decreases. For example, for a three hour time range, there is only one pixel space every three supporting points for a time step of one minute. Specifically, there are 240−180=60 free or spacing pixels left for spacing between 180 points, such that these spacing pixels can be distributed after three (180/60=3) supporting points. Similarly, for a time step of five minutes, there are 36 supporting points (180/5), or an extra 36−12=24 supporting points to be added in addition to the 12 supporting points of the 1 hr time range. This amounts to two additional supporting points between supporting point 0 and 20, for a spacing of 5, 5 and 6 pixels or at least a five pixel space between supporting points, for the three hour time range.

As the time range increases, the curves corresponding to the supporting points become crowded and distract form the overall trend. For example, and in reference to FIG. 6, for a time range of six hours and a step of one minute, there is no pixel space between supporting points, and overlap of two supporting points exists every $2^{nd}$ pixel. In contrast, for the same time range of six hours, when a time step of five minutes is used, there is still no overlap between supporting points. The number of supporting points is 72 (360/5), leaving 168 spacing pixels, which can be distributed between the 72 supporting points at a rate of 168/72=2.33, so there is a space of at least two pixels is maintained between supporting points and an extra or third spacing pixel for each interval of ten pixels. As can be seen by comparing the supporting points for three and six hours for the 5 minute time step, the supporting points 0, 6, 13, 20, etc., of the three hour time range remain also in the six hour time range.

The overlap can distort and/or obscure the overall character or trend of the graphical representation within the selected time range, as can be seen, for example, by comparing the example curves corresponding to the one-minute step and the five-minute step at the six hour range. For time ranges of twelve and 24 hours, a time step of one minute leads to superposition or clustering of multiple CGM values, and therefore decreases readability and may foster misinterpretation of the graphical representation of the CGM values.

With continued reference to FIG. 6, for a 12 hour range and one minute time step, there is overlap of three (720/240) supporting points at each pixel. For a five minute time step, there are 144 supporting points, and 240−144=96 pixels remaining to be distributed between the supporting points without moving the established location of the supporting points of the previous time range, i.e., supporting points 0, 3, 6, 10, 13, 16, 20 in each of the twelve 20-pixel wide intervals) which were established in the six hour range. Putting it another way, six additional supporting points are added in each 20-pixel interval between supporting points 0, 3, 6, 10, 13, 16, 20. The additional supporting points are added at 1, 5, 8, 11, 15 and 16 pixels.

Finally, for a twenty-four hour time range, using a one-minute time step results in overlap of six supporting points at each pixel with no spacing between pixels. Using a five minute step, although there is no spacing between pixels, overlap of just two supporting points occurs at every fifth pixel, as shown in FIG. 6. Therefore, the time step of five minutes can accommodate a 24-hour time range of CGM values with very little overlapping. Readability and comprehension of a 24-hour graphical representation of the CGM values is enhanced using the time step of 5 minutes.

In general, if the pixel width along the x-axis of the curve, i.e., the axis that represents time, is P, the time interval of which a graph is requested is H and the time step used is T, then there are N=60H/T supporting points and their pixel location is determined by (P/N)i, where i=0, 1, 2, N. When the location is not an integer, the result can be rounded to either the nearest integer or rounded down or rounded up. In FIG. 6, the result is rounded down. For example, for a step T=5 minutes, P=240 and H=12, there are N=60×12/5=144 supporting points. The first supporting point after 0 is located at (240/144) x1=1.66, which is rounded down to 1, in FIG. 6. The second supporting point after 0 is at (240/144) x2=3.33, rounded down to 3. The third supporting point after 0 is at (240/144) x3=5, and so on.

Based on the above discussion, and additionally, to save storage space and reduce processing time in the diabetes manager 104, the CGM glucose values received in a first time interval, such as a time step of one minute, are stored using a second time step or second time interval greater than the first time interval. Hereinafter, and in the interests of clarity and concreteness, the first time interval is assigned an exemplary value of one minute and the second time interval is assigned an exemplary value of five minutes, although other values can be used instead.

An entire sequence of sixty one-minute glucose values received from the CGM 200 (one hour's worth of CGM data) can be stored in a buffer for easy access. From the buffer, five consecutive CGM glucose values will be processed to determine a characteristic CGM glucose value (or five-minute grid value) for each of twelve preselected and fixed times or timestamps (grid points) of 0, 5, 10, 15, 20, 25, 30, 35, 40, 45, 50, and 55 minutes in an interval of one hour. The characteristic CGM glucose values for the twelve timestamps (grid points) will be stored in the buffer. Characteristic values for longer periods, such as the previous seven days can be stored in a memory module 410 of the diabetes manager and recalled upon request. When a request for an interval of the last six hours, for example, is made, the processor retrieves the characteristic CGM values and the supporting points of the 6 hour interval for a graphical presentation on the screen display 108.

A description of the reduction of the one-minute CGM glucose values to five-minute characteristic CGM glucose value for each timestamp for graphical representation in the display 108 of the diabetes manager 104 follows. The characteristic CGM glucose value can be selected as a composite value derived from the surrounding one-minute CGM values. The composite value can be, for example, a mean or average value, a median value, a weighted average or other modified value derived from the surrounding one-minute CGM values. Hereinafter, an exemplary characteristic value is determined as a median of the five one-minute values centered about a corresponding timestamp. The median is defined as follows:

Given a set $\{y_1; \ldots; y_n\}$ of numbers, the set $\{y_{(1)}; \ldots; y_{(n)}\}$ is the set of ordered numbers where $y_{(1)} \leq \ldots \leq y_{(n)}$ holds.

The median is defined as $$\text{median}\{y_1; \ldots; y_n\} := \begin{cases} y_{((n+1)/2)} & \text{if } n \text{ is odd,} \\ \frac{y_{(n/2)} + y_{(n/2+1)}}{2} & \text{if } n \text{ is even.} \end{cases}$$

As an example, consider the following five consecutive glucose values shown as pairs of actual time and CGM glucose values in mg/dL units (time; CGM value): (12:03; 100), (12:04; 102), (12:05; 103), (12:06; 103), and (12:07; 103). The five CGM values form an ordered set (100, 102, 103, 103, 103) with n=5. The median, as defined above, is the value at position [(5+1)/2]=3, according to the above definition. In this case, therefore, the median is 102 mg/dL. It should be appreciated that instead of the median, the average of the five of the five CGM vales can be selected as the characteristic CGM glucose value. In this example, the average CGM value is 102.2, and can be rounded down to 102 mg/dL.

Generally CGM values in the graph may be connected with straight lines, polynomial curve fitting or other interpolation.

At the very beginning of the procedure or when real-time CGM curve is requested, fewer than five one-minute CGM values may be available. If these values belong to the range of the next timestamp, these values are used to calculate the characteristic CGM glucose value for the five-minute interval surrounding the timestamp. For example, if only the following four initial datasets are available: (12:04; 102), (12:05; 103), (12:06; 103), and (12:07; 103), then the median is 103 mg/dL for the 12:05 timestamp. In contrast, if the initial values do not belong to the range of the next timestamp, these values are not used in the median calculation. For example, if only the following initial datasets are available: (12:06; 103), (12:07; 103), (12:08; 104), (12:09; 105), (12:10; 107), (12:11; 109), (12:12; 110), the first two datasets are omitted, and then the median is calculated for the next five-minute range centered around timestamp 12:10 and is 107 mg/dL for the 12:10 timestamp.

Figure 7A:
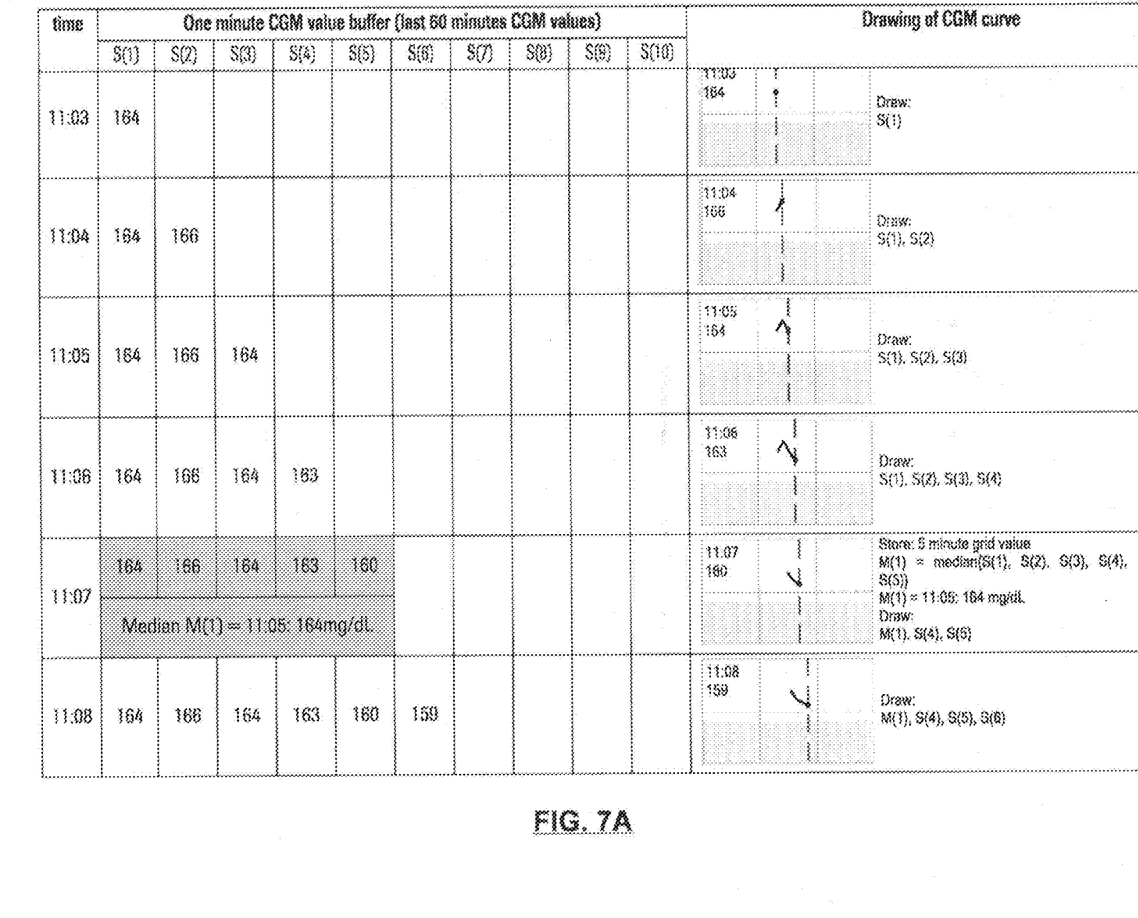
FIGS. 7A and 7B illustrate an exemplary sequence of real time drawing of the glucose measures received from a continuous glucose monitor (CGM)
Figure 7B:
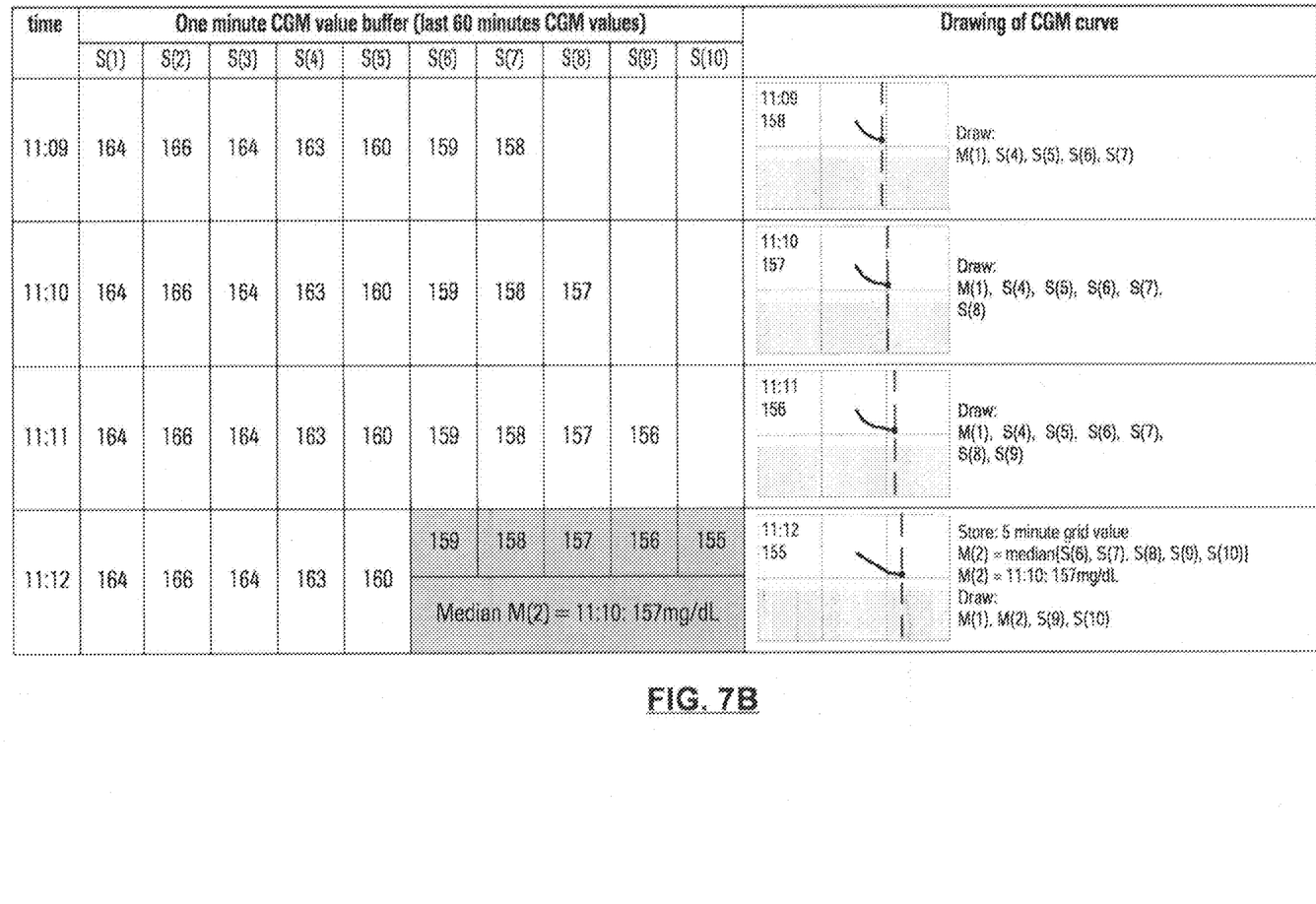

The procedure for real-time entry in the 60 minutes buffer and corresponding drawing of the CGM curve is illustrated in FIGS. 7A and 7B. The CGM one-minute data transmission process starts at 11:03 and the corresponding CGM value S(1) is placed on the graph. S(1) is equal to 164 mg/dL is the example of FIG. 7A. The drawing of the curve continues by adding the values the CGM glucose values S(2), S(3), S(4) corresponding to the next three minutes at 11:04, 11:05, 11:06 to the graph, until five CGM glucose values have been received at 11:07. At 11:07, the median M(1)=164 mg/dL of S(1), S(2), S(3), S(4) is calculated and stored for the timestamp 11:05. The CGM curve at 11:07 is drawn to include M(1) at 11:05 and the available values S(4), S(5) after 11:05. The drawing procedure continues similarly until all next five CGM glucose values S(6), S(7), S(8), S(9), S(10) are received at 11:12. The median M(2) for timestamp 11:10 is calculated from S(6), S(7), S(8), S(9), S(10) and stored. M(2) corresponds to 157 mg/DL at timestamp 11:10. The CGM curve at 11:12 is drawn to include M(1), M(2) and the CGM values after 11:10, i.e., S(9), S(10), as shown in FIG. 7B. The process continues until all the median values in an hour interval have been calculated M(1), . . . , M(12).

According to the method, the median values M(1), M(2), . . . , M(12) together with their corresponding timestamps are stored and used for calculations and graphical representations of longer than one-hour intervals. The new one-hour interval starts in the buffer and can be shown in real time, upon request. If the patient requests a CGM graph for an earlier interval, the graph is prepared from the stored median values and their timestamps for the interval.

Figure 8:
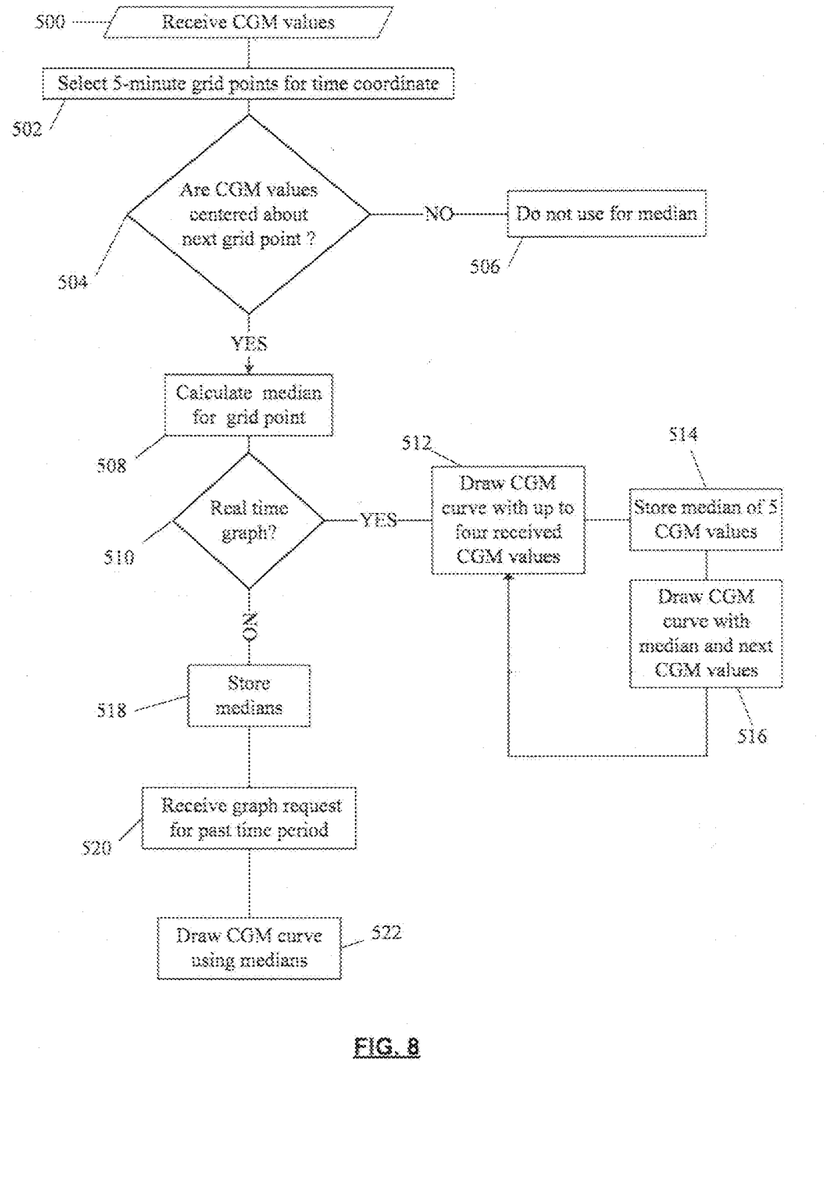
FIG. 8 is an exemplary flowchart for processing and displaying the glucose measures received from a continuous glucose monitor (CGM).

Referring to FIG. 8, a simplified flow chart illustrates the method of drawing a CGM curve on the screen display of the diabetes manager or other handheld device in communication with the CGM device, according to the method described above. The CGM values are received at a rate of one per minute (every minute) at 500, and the grid points or timestamps, separated by a five-minute interval, are selected and fixed at 502. It is determined whether a set of CGM values is centered about the nearest timestamp at 504. If not, those values are not used for calculating the median of the timestamp (grid point) at 506, otherwise the median is calculated at 508, the process continues for each of the following timestamps (grid points). If it is determined at 510, that a real time CGM curve is requested, the CGM values are plotted as they are received at 512 until five values are received and the first median is calculated and stored at the corresponding timestamp (grid point) at 514. A new CGM curve is drawn including the first median and the following CGM values at 516 and the process continues the same way for the next median, and so on. All the medians are stored at 518. When a request for a graph (CGM curve) is received for a past time period at 520, the medians are retrieved and the CGM curve is drawn for the requested period at 522.

As described above, the present teachings provide a method for processing the CGM data received at a rate of at least one per minute (or every minute) in the handheld diabetes manager such that past data can be displayed on the small screen display, while maintaining a high degree of readability and without obscuring the trend of the data. Additionally, one-hour data can be stored in a buffer and displayed in real time on demand by the patient.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer-readable medium. The computer programs may also include stored data. Non-limiting examples of the non-transitory tangible computer readable medium are nonvolatile memory, magnetic storage, and optical storage.

The broad teachings of the disclosure can be implemented in a variety of forms. Therefore, while this disclosure includes particular examples, the scope of the disclosure should not be so limited since other modifications will become apparent to the skilled practitioner upon a study of the drawings, the specification, and the following claims.

What is claimed is:

1. A method of enhancing readability of a graph showing glucose values received from a continuous glucose monitoring device (CGM) on the display of a handheld device, the method comprising:
   receiving, by the handheld device, a plurality of CGM glucose values from the continuous glucose monitoring device, where the plurality of CGM glucose values having a first fixed time interval between any two consecutive CGM glucose values;
   receiving, by the handheld device, a second time interval at which to display at least a portion of the plurality of CGM glucose values, the second time interval being greater than the first fixed time interval and being input by a user of the handheld device;
   determining, by a computer processor of the handheld device, a number of pixels on a display of the handheld device along an axis representing the second time interval;
   determining, by the computer processor, spacing between CGM glucose values to be plotted on a graph, where the spacing is a ratio between the number of pixels on the display and a number of CGM values to be displayed, such that the number of CGM values to be displayed is derived from the first fixed time interval and the second time interval;
   determining, by the computer processor, a representative glucose value for each pixel along the axis when the spacing between CGM glucose values is less than one, where each representative CGM value is derived from two or more received CGM values;
   displaying, by the computer processor, the representative glucose values on the display of the handheld device, the representative glucose value being displayed along the axis of the graph when the spacing between CGM glucose values is less than one: and
   displaying, by the computer processor, the plurality of CGM glucose values on the display of the handheld device, the plurality of CGM glucose values being displayed along the axis of the graph when the spacing between CGM glucose values is more than one.

2. The method of claim 1, wherein each representative glucose value is the median of received CGM glucose values centered about the preselected fixed time for each second time interval.

3. The method of claim 1, wherein the first fixed time interval is one minute and the second time interval is five minutes.

4. The method of claim 1, further comprising storing the representative glucose values at the corresponding preselected fixed times in a memory module of the handheld device.

5. The method of claim 1, further comprising storing the received CGM glucose values and the representative glucose values in a buffer for a sixty minute time interval.

6. The method of claim 5, further comprising displaying a CGM glucose curve in real time on the handheld device.

7. The method of claim 6, further comprising omitting from the CGM glucose curve initial received CGM values not belonging to the second interval that is centered about the predetermined fixed time when determining the representative glucose value of the second time interval.

8. The method of claim 6, further comprising displaying in the CGM curve the determined characteristic CGM value and the subsequent received CGM values up to the determination of a next characteristic CGM value.

9. The method of claim 1, further comprising determining a plurality of supporting pixel points for displaying the representative glucose values on a CGM glucose curve of a requested time period for display on the handheld device from a pixel width of the graph and a time period to be displayed.

10. A method of enhancing readability of glucose measures on a display of a handheld device, comprising:
    receiving, by the handheld device, a plurality of glucose measurements values, where the plurality of glucose measurement values have a fixed time interval between each of the glucose measurement values;
    receiving, by the handheld device, a time period over which to display the plurality of glucose measurement values, the time period being greater than the fixed time interval and being input by a user of the handheld device;

determining, by a computer processor of the handheld device, a number of pixels along an axis on a display of the handheld device which correlates to the time period;

determining, by the computer processor, spacing between the plurality of glucose measurement values to be plotted on the display by multiplying the number of pixels by the fixed time interval to yield a product and dividing the product by the time period;

determining, by the computer processor, a representative glucose value for each pixel along the axis in response to a determination that the spacing between the plurality of glucose measurement values is less than one, each representative glucose value being derived from two or more glucose measurement values;

displaying, by the computer processor, the representative glucose values along the axis in response to a determination that the spacing between the plurality of glucose measurement values is less than one; and displaying, by the computer processor, the plurality of glucose measurement values along the axis in response to a determination that the spacing between the glucose measurement values is one or more than one.

11. A handheld diabetes management device, comprising:
a display;
a communications module configured to receive a plurality of glucose measurements values, where the plurality of glucose measurement values have a fixed time interval between each of the glucose measurement values;
a user interface module configured to receive a time period over which to display the plurality of glucose measurement values, the time period being greater than the fixed time interval and being input by a user of the handheld device;
a processing module interfaced with the communications module and the user interface module to determine a number of pixels along an axis on a display of the handheld device which correlates to the time period and to determine spacing between the plurality of glucose measurement values, where the spacing is a ratio between the number of pixels and a number of values to be displayed and the number of values to be display is derived from the fixed time interval and the time period;
the processing module cooperatively operable with the display to display a representative glucose value at each pixel along the axis in response to a determination that the spacing between the plurality of glucose measurement values is less than one, each representative glucose value being derived from two or more glucose measurement values, and to display the plurality of glucose measurement values along the axis in response to a determination that the spacing between the glucose measurement values is one or more than one, where the user interface module and the processing module are implemented by computer readable instructions executed by a computer processor residing in the device.

12. The handheld diabetes management device of claim 11 further comprises a port configured to receive a test strip for blood glucose measurement; and a blood glucose measurement module cooperatively operable with a test strip inserted in the port for blood glucose measurement.

* * * * *